United States Patent [19]

Bebbington et al.

[11] Patent Number: 5,747,308
[45] Date of Patent: May 5, 1998

[54] RECOMBINANT DNA METHOD

[75] Inventors: **Christopher Robert Bebbington;
Geoffrey Thomas Yarranton**, both of
Berkshire, United Kingdom

[73] Assignee: Celltech Therapeutics Limited,
Berkshire, United Kingdom

[21] Appl. No.: 385,063

[22] Filed: Feb. 7, 1995

Related U.S. Application Data

[63] Continuation of Ser. No. 234,596, Apr. 28, 1994, abandoned, which is a continuation of Ser. No. 100,345, Aug. 2, 1993, abandoned, which is a continuation of Ser. No. 848,965, Apr. 27, 1992, abandoned.

[30] Foreign Application Priority Data

Oct. 25, 1989 [GB] United Kingdom ............ 8924021
Oct. 25, 1990 [WO] WIPO ............ WOX/GB90/01640

[51] Int. Cl.$^6$ ............ C12N 15/00; C12N 5/06;
C12N 15/85; C12P 21/06
[52] U.S. Cl. ............ 435/172.3; 435/326; 435/372.1;
435/69.1; 435/320.1
[58] Field of Search ............ 435/69.1, 70.1,
435/172.3, 320.1, 240.1, 326, 372.1

[56] References Cited

U.S. PATENT DOCUMENTS 5,122,464   6/1992   Wilson et al. ............ 435/172.3

FOREIGN PATENT DOCUMENTS 0 319 206   11/1988   European Pat. Off. .
WO86/05807  10/1986   WIPO .
WO87/04462   7/1987   WIPO .
WO89/10404  11/1989   WIPO .

OTHER PUBLICATIONS

Brown et al. 1987, Cell vol. 49 pp. 603–612.
Roberts et al, "Gene Amplification and Gene Correction in Somatic Cells", *Cell*, 29:109–119, (1982).
Israel et al, "Highly Inducible Expression From Vectors Containing Multiple GRE's in CHO Cells Overexpressing The Glucocorticoid Receptor," *Nucleic Acids Research*, 17:4589–4603, (1989).
Bebbington et al, "The Use of Vectors Based on Gene Amplification For The Expression of Cloned Genes in Mammalian Cells," *DNA Cloning*, 3:163–188, (1987).
Hayward et al, "The Cloning And Nucleotide Sequence of CDNA For An Amplified Glutamine Synthetase Gene From The Chinese Hamster," *Nucleic Acids Research*, 14:999–1008, (1986).

*Primary Examiner*—Nancy T. Vogel
*Attorney, Agent, or Firm*—Foley & Lardner

[57] ABSTRACT

There is described a method for obtaining a eukaryotic cell containing in its DNA multiple copies of a GS gene, comprising: transforming a eukaryotic glutamine auxotroph with a GS gene; selecting transformant cells containing the GS gene; and culturing the selected transformant cells in a medium which lacks glutamine or in which the amount of glutamine is progressively depleted, the GS gene being of a character such that, or the conditions employed during the culturing step being such that, the GS gene is so weakly transcribed that the cells in which the GS gene has been amplified are selected.

13 Claims, 3 Drawing Sheets

RECOMBINANT DNA METHOD

This application is a continuation of application Ser. No. 08/234,596, filed Apr. 28, 1994 (now abandoned) which is a continuation of Ser. No. 08/100,345, filed Aug. 2, 1993 (now abandoned), which is a continuation of Ser. No. 07/848,965, filed Apr. 27, 1992 (now abandoned).

The present invention relates to a process for obtaining a eukaryotic cell containing in its DNA multiple copies of a glutamine synthetase (GS) gene. Preferably, the cell thus produced also contains multiple copies of a heterologous gene.

By "gene" is meant one or more DNA sequences containing sections encoding a desired protein and all the necessary upstream and downstream sequences to allow the protein to be expressed in a host cell. By "heterologous gene" is meant a gene which encodes a protein not normally synthesised by the host cell into which it is introduced. Generally, a heterologous gene will be introduced into the host cell line by transformation with one or more vectors into which the heterologous gene has been cloned. The vectors may be, for instance, viral or plasmid vectors.

The ability of cloned heterologous genes to function when introduced into a host cell has proved to be invaluable in studies of gene expression. It has also provided a means of obtaining large quantities of polypeptides which are otherwise scarce or which are completely novel products of gene manipulation. It is advantageous to obtain such polypeptides from a mammalian cell since polypeptides produced in such a cell are generally correctly folded, appropriately modified and completely functional, often in marked contrast to those polypeptides when expressed in a bacterial cell.

Where large amounts of product are required, it is necessary to identify cell clones in which the vector sequences are retained during cell proliferation. Such stable vector maintenance can be achieved either by use of a viral replicon or as a consequence of integration of the vector into the host cell DNA.

Where the vector has been integrated into the host cell's DNA, the copy number of vector DNA, and concomitantly the amount of polypeptide which could be expressed, can be increased by selecting for cells in which the vector sequences have been amplified after integration into the host cell DNA.

A known method for carrying out such a selection procedure is to transform a host cell with a vector comprising a gene which encodes an enzyme which is inhibited by a known drug. The vector may also comprise a heterologous gene. Alternatively, the host cell may be co-transformed with a second vector which comprises the heterologous gene.

The transformed or co-transformed host cell is then cultured in increasing concentrations of the known drug thereby selecting drug-resistant cells. It has been found that one common mechanism leading to the appearance of mutant cells which can survive in the increased concentrations of the otherwise toxic drug is the over-production of the enzyme which is inhibited by the drug. This most commonly results from increased levels of its particular mRNA, which in turn is frequently caused by amplification of vector DNA and hence gene copy number.

It has been found that, where drug resistance is caused by an increase in copy number of the gene encoding the inhibitable enzyme, there is a concomitant increase in the copy number of the heterologous gene in the host cell's DNA. There is thus an increased level of production of the desired polypeptide.

The most commonly used system for such co-amplification uses dihydrofolate reductase (DHFR) as the enzyme which can be inhibited. This can be inhibited by the drug methotrexate (MTX). To achieve co-amplification, a host cell which lacks an active DHFR gene is either transformed with a vector which comprises a DHFR gene and a heterologous gene or co-transformed with a vector comprising a DHFR gene and a vector comprising a heterologous gene. The transformed or co-transformed host cell is cultured in media containing increasing levels of MTX and those cell lines which survive are selected.

Another system, described in [1], for producing co-amplification uses GS as the inhibitable enzyme and methionine sulphoximine (Msx) (among others) as the inhibitor. It is suggested in [1] that the GS gene should include a regulatable promoter which is switched up during selection and amplification and subsequently down-regulated. (In this description, numerals in square brackets refer to prior art documents. These are listed in numerical order at the end of the description).

Another system for obtaining gene amplification is disclosed in [2], which relates to improved means for obtaining enhanced production of proteins encoded by structural genes fortuitous of interest in a host. The disclosure in [2] is based on transfecting the host with an expression vector comprising a wild-type amplifiable gene and a predetermined structural gene. The host is typically not complemented by the amplifiable gene product. If desired, another selection marker may be utilized to select a desired population of cells prior to the amplification.

Some years ago Roberts and Axel [3] described experiments in which aprt⁻ tk⁻ L cells were transformed with a plasmid containing a wild-type aprt gene and a truncated, promoterless tk gene. Initial transformants that integrated a single copy of this plasmid exhibited the aprt⁺ phenotype but remained tk⁻. Subsequently, tk⁺ variants emerged, resulting from a 20 to 50 fold amplification of the linked plasmid and flanking DNA sequences, presumably involving fortuitous gene rearrangements which activated the promoterless tk gene. Similar to current co-amplification systems, the experiments described in [3] were carried out using host cells which lack genes encoding the aprt and tk enzymes. There are relatively few such cell lines available.

The co-amplification systems which are at present available suffer from some disadvantages. For instance, it is generally necessary to use a host cell which lacks an active gene encoding the enzyme which can be inhibited. This tends to limit the number of cell lines which can be used with any particular co-amplification system. For instance, DHFR deficient mutants are only available for Chinese Hamster Ovary (CHO) cell lines. Also, all of the known systems use a toxic inhibitor; for instance, MTX for DHFR systems and aminopterin for the procedure described in [3].

In this respect the GS system is more useful in that a variety of lymphoid cell types, including myeloma cells, need to be grown in media containing glutamine but can be converted to glutamine independent growth by transfection of a cloned GS gene. It has also been observed that lymphoid cells such as myeloma cells only spontaneously mutate to glutamine independence at very low frequency. Thus, lymphoid cells such as myeloma cells can be used in selection and amplification experiments wherein a heterologous GS gene is used as the selection and amplification marker. Furthermore, such lymphoid cells are particularly advantageous for use in industrial production processes in view of their ability to grow well in fermenters and efficiently secrete products such as antibodies.

However, in the selection and amplification protocols so far suggested for the GS system, as for other similar systems, the enzyme inhibitor is present during both the selection and the amplification steps. It is well known that most of the inhibitors used, and in particular MTX and Msx, are toxic. Thus, in carrying out the selection and amplification steps, it is necessary to use toxic reagents, with the concomitant health hazard.

Moreover, once the amplification has been carried out, it is generally necessary to retain the toxic inhibitor in the culture medium. If this is not done, it often happens that the gene encoding the inhibitable enzyme is deleted from the cell DNA. When this occurs, the heterologous gene is also deleted, thus reversing the effects of the amplification. If the toxic inhibitor is retained in the medium, it will be necessary to purify carefully the desired protein, especially if it has a therapeutic use, so as to ensure that it is safe to use.

It would therefore be desirable to be able to provide a method for obtaining a cell containing in its DNA multiple copies of a GS gene without having to use excessive or any amounts of toxic inhibitors. This system could then be used to co-amplify heterologous genes.

Accordingly, in a first aspect the present invention provides a method for obtaining a eukaryotic cell containing in its DNA multiple copies of a GS gene comprising:

transforming a eukaryotic glutamine auxotroph with a GS gene;

selecting transformant cells containing said GS gene; and culturing the selected transformant cells in a medium which lacks glutamine or in which the amount of glutamine is progressively depleted;

the GS gene being of a character such that, or the conditions employed during culturing being such that, the GS gene is so weakly transcribed that cells in which the GS gene has been amplified are selected.

Weak transcription of the GS gene during culturing may be achieved by use of a constitutively weak promoter with the GS coding sequence, typically in combination with an additional selectable marker to select for transformants. Alternatively, a regulatable promoter may be used with a GS coding sequence to provide relatively strong GS transcription for selection of transformants and relatively weak, down-regulated transcription of GS for selection of cells in which the GS gene has been amplified.

Thus in a first embodiment of the first aspect of the present invention, there is provided a method for obtaining a eukaryotic cell containing in its DNA multiple copies of a GS gene, which method comprises:

transforming a eukaryotic glutamine auxotroph with a GS gene, wherein the GS coding sequence is under the control of a weak promoter, and a gene for a selectable marker;

selecting for transformant cells by use of the selectable marker in a medium containing glutamine; and culturing the selected transformant cells in a medium which lacks glutamine or in which the amount of glutamine is progressively depleted, thereby to select cells in which the GS gene has been amplified.

The selectable marker gene may be any of the known marker genes, such as the neo, dhfr, gpt, hmb and CAD genes. Preferably, the selectable marker gene is the neo gene, or a neo gene the bacterial promoter sequence of which has been deleted (herein referred to as ne), either of which confers on transformant cells resistance to the antibiotics kanamycin, neomycin and G418.

The GS gene and the selectable marker gene are preferably located on a single vector, such as a plasmid or a viral vector.

Suitable promoters for the GS gene are the SV40 early, SV40 late, MMLV-LTR, MMT-1 and MMTV promoters. Preferably, the promoter is the SV40 early or SV40 late promoter.

In this embodiment of the invention, once transformants have been selected, they will not be able to survive in a glutamine-free medium, despite the presence of an exogenous GS gene. Since the exogenous GS gene is under the control of a weak promoter, normally it will not be able to produce sufficient GS to allow survival. Thus, only variant cells in which the GS gene has been amplified will survive. Occasionally transformed cell lines may be identified which are able to grow in the absence of glutamine as a result either of integration of the exogenous GS gene into a particularly active site in the genome, or of integration of multiple copies of the exogenous GS gene. Such cell lines are not suitable for use in the method of the invention, and may be identified by their high frequency of survival, e.g. approaching 100% survival, when selected in glutamine-free medium.

In a second embodiment of the first aspect of the present invention, there is provided a method for obtaining a eukaryotic cell containing in its DNA multiple copies of a GS gene, which method comprises:

transforming a eukaryotic glutamine auxotroph with a GS gene, wherein the GS coding sequence is under the control of a regulatable promoter;

culturing transformed cells in a medium containing glutamine;

selecting for transformant cells by culturing the cells in a glutamine-free medium under conditions which cause the promoter to be up-regulated; and culturing the selected transformed cells in a glutamine-free medium under conditions which cause the promoter to be down-regulated, thereby to select cells in which the GS gene has been amplified.

Regulatable promoters are well known in the art of recombinant DNA technology and any of these known promoters may be used in this embodiment of the present invention. Selection and regulation of a suitable promoter will generally be a matter well within the ordinary competence of the skilled person.

Suitable regulatable promoters for mammalian cells include those containing serum response elements (SRE), interferon response elements (IRE), glucocorticoid response elements (GRE), metal response elements (MRE), retinoic acid response elements (RARE), oestrogen response elements (OERE), androgen response elements (ARE), thyroid hormone response elements (THRE), phorbol ester (e.g. TPA) response elements (TRE), activating transcription factor (ATF) binding sites, cyclic-AMP response elements (CRE), heat-shock response elements (HSE), stress or glucose-regulated elements and *E. coli.* lac operator elements.

A specific example of a regulatable promoter which may be used is a eukaryotic promoter in which the bacterial lac operator sequences have been inserted. This promoter can be up-regulated by the inclusion in the medium of isopropylthiogalactoside (IPTG), provided the cell line is also co-transformed with a lac repressor gene. In this case, the transformation medium will, and the culturing medium will not, contain IPTG.

It is well known that regulatable promoters are not effectively regulatable in all cell types. Thus, it is necessary to select a promoter which is suitable for the cell type selected. For instance, GRE-containing promoters can be used in fibroblasts and cell lines derived therefrom as these cell types contain glucocorticoid receptors. However, GRE-containing promoters are insufficiently regulatable in lymphoid cells as such cells lack glucocorticoid receptors. Also metallothionein-containing promoters are generally insufficiently regulatable in lymphoid cells.

If a cell type is selected for which no suitable regulatable promoter is available, it is possible to transform the cell type to make it suitable for use with a regulatable promoter. For instance, a cell line can be transformed with a gene which encodes a glucocorticoid receptor. This transformed cell line will then be suitable for use with a GRE-containing promoter to direct GS expression. The development of an inducible expression system based upon GREs and over expression of glucocorticoid receptor in CHO cells is described in [4]. An even more suitable system is to express the glucocorticoid receptor from a GRE-containing promoter. This may lead to very tight regulation of the GS gene in media which lack GRE inducing agents.

This second embodiment of the invention is equivalent to the first embodiment in that the GS gene with the up-regulated promoter acts as a selectable marker, endowing transformed cells with the ability to survive in the glutamine-free medium. Once the promoter has been down-regulated, there will typically not be enough glutamine produced to enable even the transformed cells to survive in a glutamine-free medium. It will be necessary to screen transformants for those which fail to grow in glutamine free medium. Such cells can be used to select for rare variants in which the GS gene has been amplified and which will be able to survive in a glutamine-free medium.

Preferably, the glutamine auxotroph which is to be transformed is one which does not contain an active or a sufficiently active GS gene, such as a lymphoid cell line. Additionally, it will be appreciated that the glutamine auxotroph used should have a low frequency for generation of glutamine independent variants, e.g. preferably a frequency of less than 1 in $10^5$. Lymphoid cell lines include myeloma or hybridoma cell lines, T cells, and immortalised T cells. Preferred cell lines are myeloma cell lines, advantageously of mouse or rat origin. Particularly preferred cell lines are the NSO, IR983F and P3-X63.Ag8.653 lines.

If such a cell line is used, any untransformed cell lines will die off during culture in a medium which lacks glutamine, which is essential for their survival. During the selection stage in the second embodiment of the invention, any transformed cell lines containing even low copy numbers of the GS gene will be able to produce sufficient GS to survive because of the up-regulation of the promoter. This will ensure that enough GS is expressed from the GS gene to enable production of enough glutamine to sustain the life of the cells in the absence of glutamine in the medium.

In the amplification step (in the second embodiment where the promoter will be down-regulated), there are only a few copies of the GS gene in a transformed cell line, and it will not be possible for it to produce enough glutamine from the substrate available to enable the cell to survive. However, if multiple copies of the GS gene are present in the cell line (as will be the case when amplification has occurred), the multiple GS gene copies will provide enough GS expression to enable the substrate to be converted to glutamine in sufficient quantities to enable the cell line to survive.

It is possible, but not preferred, to use cell lines, such as the chinese hamster ovary (CHO) cell line, which have an active GS gene. However, in this case, it will be necessary to carry out the transformation and culturing steps in a medium containing sufficient Msx (or other GS inhibitor) to inhibit substantially all endogenous GS activity. Thus, any cell which is not transformed will not be able to survive the transformation stage due to the presence in the culture medium of the GS inhibitor. Moreover, once the regulatable promoter has been down-regulated, only those cells in which there are multiple copies of the vector GS gene will be able to survive on the limited amount of substrate present in the glutamine-free medium.

Preferably, the transformed cells which survive culturing in a glutamine-free medium, and which therefore contain multiple copies of the vector GS gene, are further cultured in a glutamine-free medium containing a substrate which can be converted to glutamine by a pathway involving GS, if necessary under conditions which cause the regulatable promoter to be down-regulated. By doing this, the selection pressure for multiple copies of the GS gene will be maintained and there will therefore be less likelihood of the excess copies of the GS gene being eliminated from the host cell DNA.

Advantageously, the GS gene system of the present invention will be used in order to enable a heterologous gene to be co-amplified with the GS gene. Therefore, it is preferred that the eukaryotic cell is transformed either with a vector containing both the GS gene and a heterologous gene or with separate vectors respectively and separately containing the GS gene and the heterologous gene.

The heterologous gene may encode a single chain protein (although such a single chain protein may be cleaved after expression to produce a multiple chain protein) such as tissue plasminogen activator (tPA), tissue inhibitor of metalloproteinase (TIMP), or human (or other animal) growth hormone (hGH). Alternatively, the heterologous gene may encode a multiple chain protein the chains of which are expressed separately and then assembled after expression.

A particularly preferred heterologous gene encodes an immunoglobulin (Ig) molecule or a fragment or analogue thereof (an Ig-type molecule). For an Ig or Ig-type molecule, the sequences encoding the heavy and light chains may be present on the same or on separate vectors. The GS gene may be present on one of the vectors containing the heavy or light chain encoding sequence, if they are on separate vectors, or may be on an entirely separate vector. However, it is preferred that the GS gene and the sequences encoding both the heavy and the light chains of the Ig or Ig-type molecule are all present on the same vector.

Advantageously, the heavy and light chain genes are each under the control of a strong promoter, such as the human cytomegalovirus (hCMV) promoter and the GS gene is located upstream of one of the strong promoters, the other strong promoter being arranged on the vector to direct expression in the opposite direction to the GS and first strong promoters. In an alternative arrangement, the heavy and light chain genes are each under control of a strong promoter, and both of these strong promoters and associated genes are located in tandem downstream of the GS gene.

As a general rule, host cells used in recombinant DNA technology are transformed and cultured in media containing up to 4 mM glutamine and a source of other nutrients, protein and tonicity agents, such as foetal calf serum (FCS). Any of the known media can be used as the basis for the media used in the process of the present invention. However, it will have to be insured that in the final culturing step the media are substantially glutamine-free.

Moreover, the media will normally need to contain asparagine. An example of a suitable glutamine-free medium is G-DMEM which is described in [5].

The invention thus provides methods for obtaining cells which contain in their DNA multiple copies of a GS gene without having to use excessive or any amounts of toxic inhibitor. In particular, however, multiple copies of the GS gene and corresponding multiple copies of desired heterologous genes may be maintained in the DNA of transformant cells during growth and culturing without need to use toxic inhibitors. This is particularly desirable for cell culture production processes, not only to avoid the dangers inherent in using toxic inhibitors but also to avoid the need to carefully remove the inhibitor during purification of the desired protein.

Accordingly in a further aspect the invention provides a method for maintaining multiple copies of a GS gene in the DNA of transformant eucaryotic host cells comprising culturing the transformant cells in a medium which lacks glutamine, the GS gene being of a character such that, or the conditions employed during culturing being such that, the GS gene is so weakly transcribed that cells containing the multiple copies of the GS gene are selected over cells in which copies of the GS gene have been eliminated from the host cell DNA.

The transformant cell line used in the method of this further aspect of the invention may be obtained by any appropriate means. For example, toxic inhibitors e.g. Msx may be used to select for transformant cells containing the multiple copies of the GS gene. Also toxic inhibitors may be used to select for transformants after initial transfection with GS as in the second embodiment of the aspect of the invention first described above. Preferably the transformant cell line used is prepared by the method of the first aspect of the invention.

The present invention also includes vectors for use in both embodiments of the present invention and host cells transformed by the process of the present invention. In particular, the present invention includes vectors containing a GS gene wherein the GS encoding sequence is under the control of a eukaryotic promoter containing a lac operator or a GRE-containing promoter. Preferably, such vectors also contain a heterologous gene, most preferably encoding an Ig or Ig-type molecule. Preferred transformed cells are those derived by transformation of a myeloma cell with a vector as described above.

The present invention is now described by way of example only with reference to the accompanying drawing in which.

Figure 2:
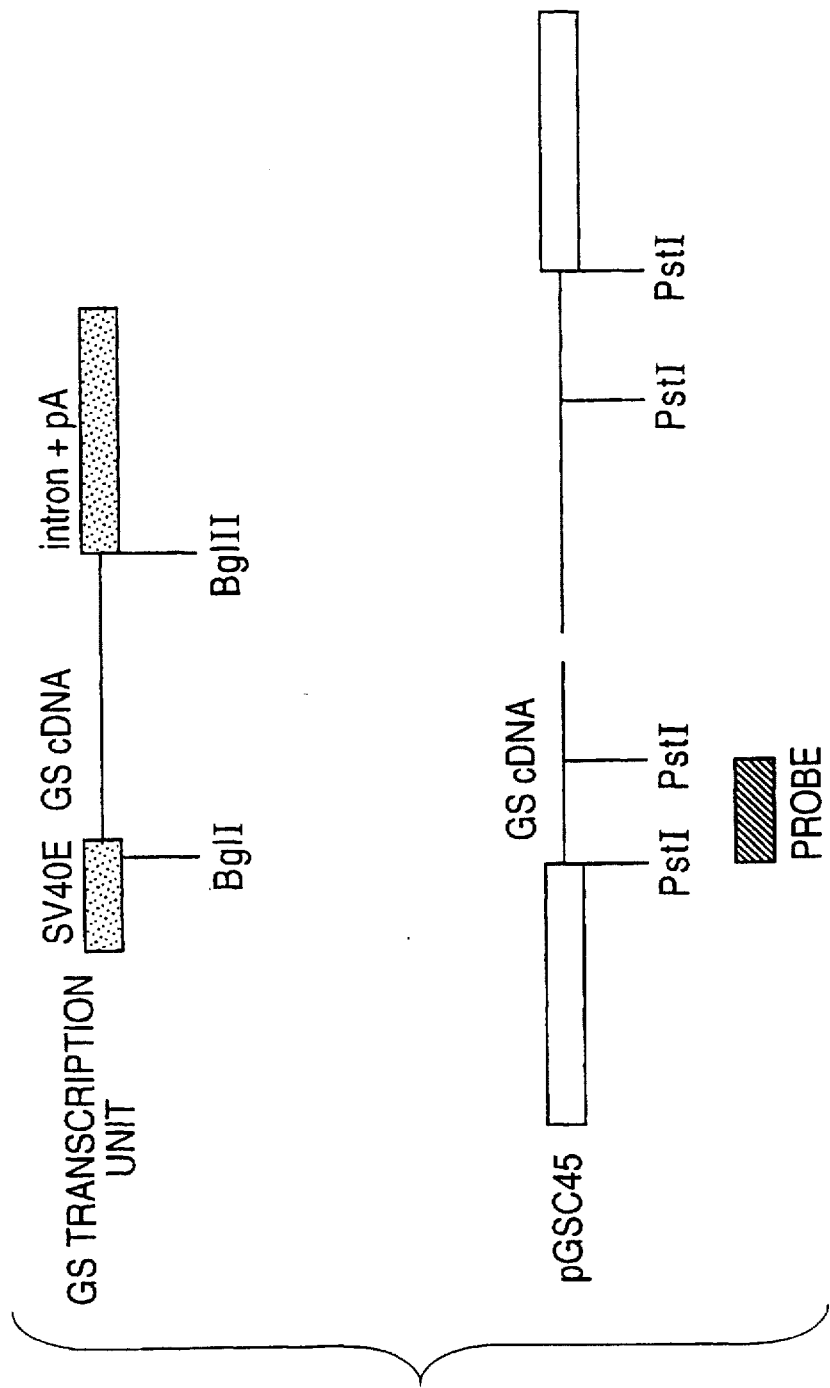
FIG. 2 shows a GS transcription unit derived from pSV2.GS, which is present in pRS3GSne13, pRS3GSne18 and pST-6, and plasmid pGSC45 on which is indicated the PstI fragment used as a probe for detection of GS-encoding sequences on Southern blots.

In FIG. 2, filled boxes represent SV40 sequences and the thin line represents hamster GS cDNA sequences. The GS sequences in the two halves of the Figure are aligned.

Plasmid Construction

Figure 1:
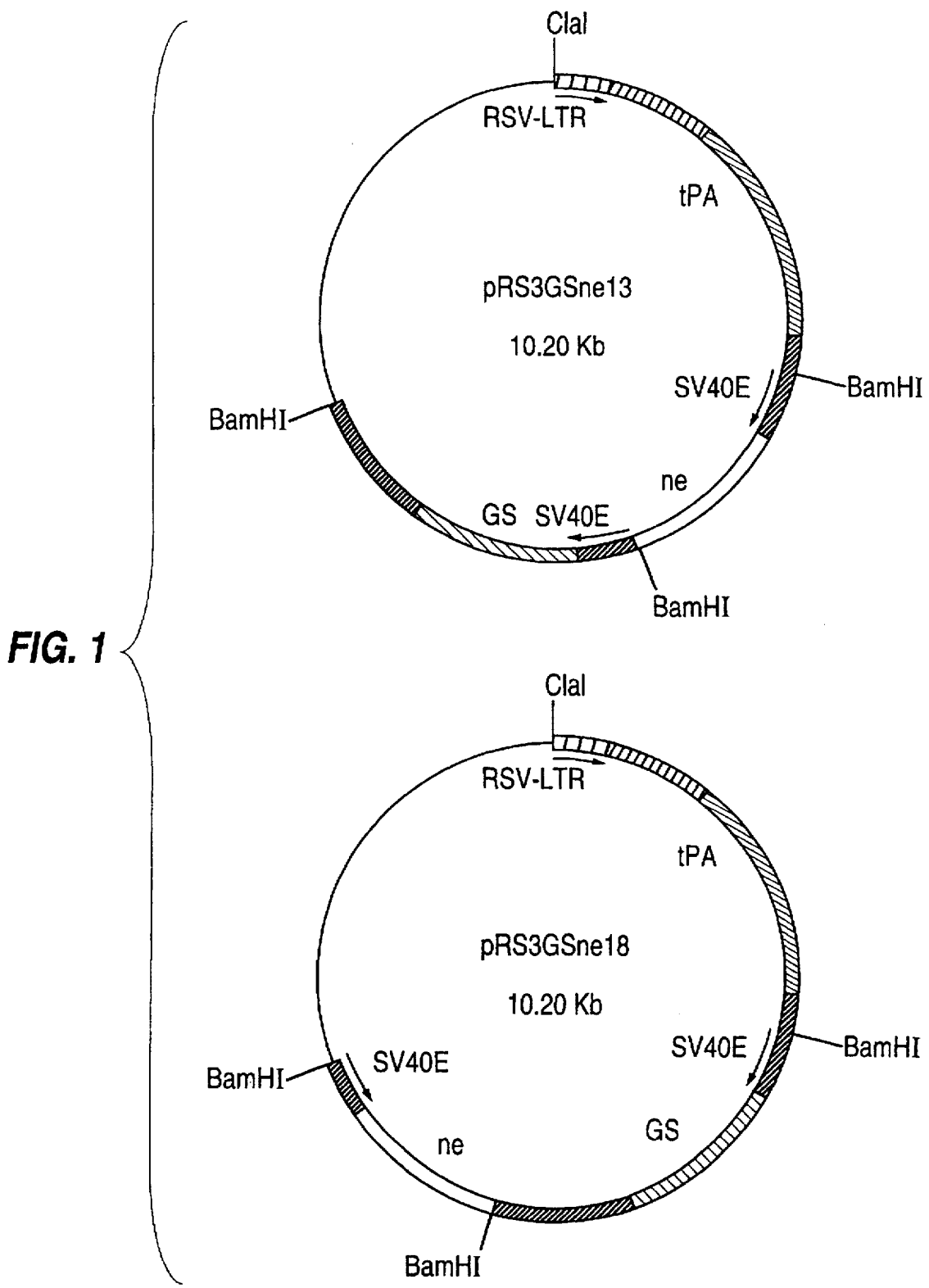
FIG. 1 shows a restriction map of plasmid pRS3GSne13 and a restriction map of plasmid pRS3GSne18.

Plasmids pRS3GSne13 and pRS3GSne18 were constructed as follows. A GS transcription unit was isolated from plasmid pSV2.GS [6] as a 2.4 kb PvuII-BamHI fragment. Bam-HI linkers were added to the PvuII site in the 2.4 kb fragment, and the linked fragment was inserted into the single BamHI site in plasmid pRSV3 which contains a transcription unit for tissue plasminogen activator (tPA). This produced plasmid pRS3GS [7] in which the tPA and GS genes are transcribed in the same orientation. A ne gene was then isolated as a 1.5 kb fragment from pSV3Bne [7] and inserted into one of the two BamHI sites in plasmid pRS3GS after partial digestion of the plasmid with BamHI. Two plasmids were isolated from this ligation. The first, pRS3GSne13, had the ne gene inserted downstream of the GS gene. The second, pRS3GSne18, had the ne gene inserted between the tPA gene and the GS gene. The structures of these two plasmids are shown in FIG. 1.

Plasmid pRS3GSne18 contains a cDNA sequence encoding tPA under the control of the promoter from the Rous sarcoma virus long terminal repeat (RSV-LTR), a selectable marker and an amplifiable gene. The marker is the ne gene which confers resistance to the antibiotic G418. The amplifiable gene is the GS gene, in which the GS coding sequence is under the control of the SV40 early (SV40E) promoter and SV40 splicing and polyadenylation signals.

Figure 3:
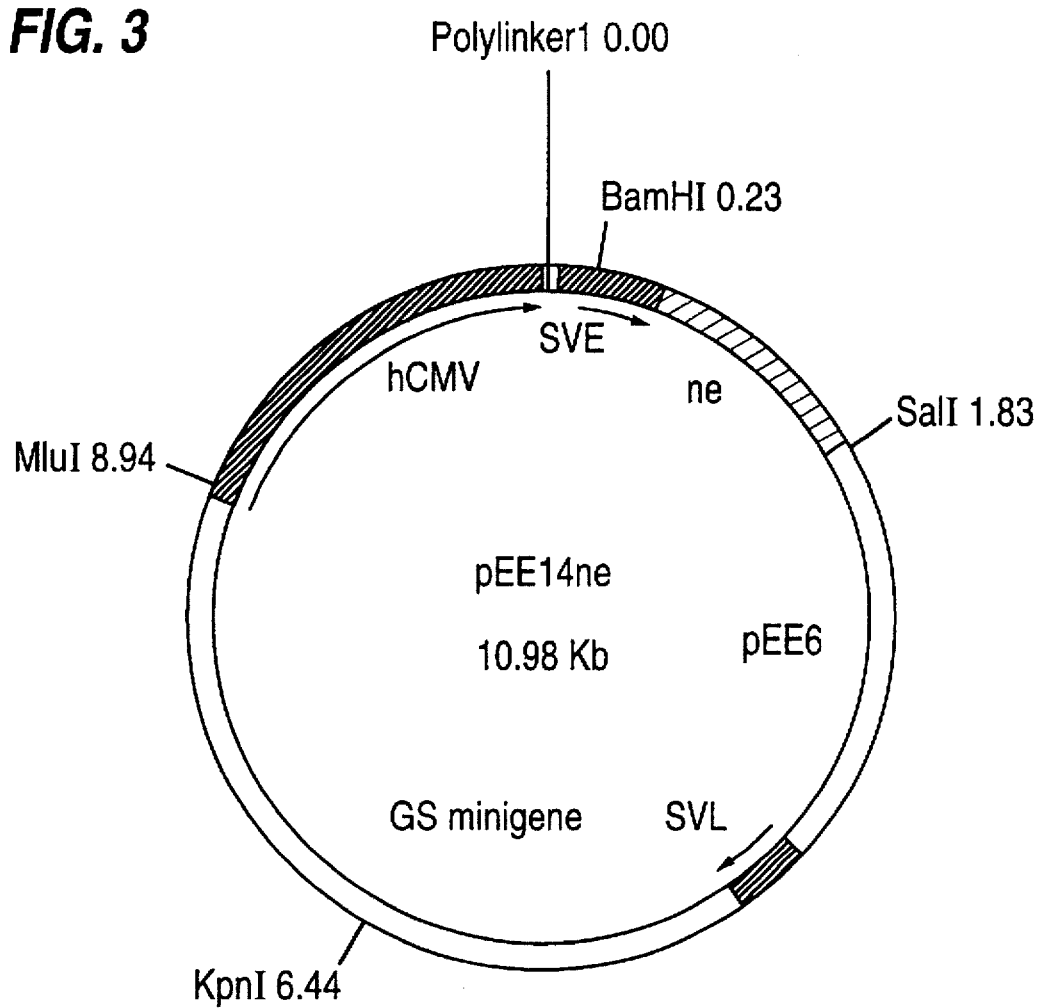
FIG. 3 shows a restriction map of plasmid pEE14ne.

An alternative vector, called pEE14ne, which permits selection for GS-gene amplification with a toxic inhibitor, was constructed and is shown in FIG. 3. It contains a derivative of the GS minigene under the control of the SV40 Late promoter from pSVLGS.1 [6] in a plasmid vector pEE6. Also present is the SV40 Early-ne transcription unit identical to that in pRS3GSne13 and pRS3GSne18 described above.

pEE14ne was constructed as follows. The HindIII site at the 5' end of the SV40 Late promoter in pSVLGS.1 [6] was converted to a BamHI site by partial digestion of pSVLGS.1 with HindIII and ligation of an oligonucleotide HindIII - BAmHI adaptor. Small-scale plasmid preparations of a number of bacterial transformants were screened for conversion of the appropriate site. The resulting plasmid is pSVLGS.2. The two remaining HindIII sites in the GS minigene were then destroyed by digestion of pSVLGS.2 with HindIII, isolation of both fragments, filling in the cohesive ends with DNA polymerase I and re-ligation to create pSVlGS.3. The EcoRI site in the GS-coding region was removed by site-directed mutagenesis in M13, converting a T to a C using the oligonucleotide (SEQ ID NO:1):
5'- C T A T T T G G A A C̲ T C C C A C T G G - 3'
(where the nucleotide underlined is the site of the point mutation).

A Kpn-EcoRV fragment containing the mutated EcoRI site from M13 was then used to replace the corresponding Kpn-EcoRV fragment in pSVLGS.3 to create pSVLGS.4. The remaining EcoRI site at the 5' end of the GS minigene was deleted by digestion of pSVLGS.4 with EcoRI, filling in the ends with DNA polymerase I and religation to form pSVLGS.5. The 4.8 kb BamHI fragment of pSVLGS.5 containing the SV40L-GS minigene transcription unit was then inserted at the BglII site of pEE6hCMV-BglII [5] to form pEE14. A ne gene under the control of the SV40 Early promoter from pSV3Bne was inserted, after conversion by standard techniques of the 3' BamHI site to a SalI site, between the BamHI and SalI sites of pEE14 to create pEE14ne. pGSC45 has been described in [8].

EXAMPLE 1

Plasmid pRS3GSne18 was introduced into the mouse myeloma cell line NS0 by electroporation using a Biorad "Gene Pulser" apparatus, essentially according to the manufacturer's instructions. $10^7$ cells were subjected to two pulses of 1500 volts at 3 µF in the presence of 40 µg of circular plasmid DNA.

The cells were then plated out at various densities in 96-well tissue-culture trays in non-selective medium (DMEM with 2 mM glutamine and 10% FCS). After 24 hours, antibiotic G418 was added to a final concentration of 1 mg/ml to select for cells which were expressing the ne gene. 15 days later, viable colonies were counted. The transfection efficiency was approximately 1 colony per $10^4$ cells transfected.

Cells from 17 wells (A1 to A6, B1 to B6 and C1 to C5) which contained only a single viable colony were then expanded separately in culture and frozen stocks were secured. Each of these 17 G418-resistant cell lines was then tested for the ability to grow without glutamine by distributing cells in wells of a 24-well plate at a density of approximately $5 \times 10^5$ cells per well in 0.5 ml DMEM+10% FCS+2 mM glutamine.

To each well was then added 1 ml of G-DMEM, a glutamine-free DMEM medium containing non-essential amino acids (including glutamate and asparagine). G-DMEM is described in [5]. This procedure allows the cells gradually to deplete the medium of glutamine. Thereafter, the cells were transferred to G-DMEM.

Each of the 17 cell lines tested showed extensive cell death within 4 to 5 days under this selection procedure, indicating that in most cells the GS gene was not expressed or was expressed in each cell at too low a level to allow glutamine-independent growth. Despite this substantial cell death, after 2 to 3 weeks of culture in G-DMEM, small viable colonies were noted in culture wells of five of the cell lines (cell lines A1, B1, B5, B6 and C3). The frequency with which such colonies arose varied depending on the cell line and was between 1 and 20 colonies per $10^5$ cells plated. In contrast, control NS0 cells plated under the same conditions showed no glutamine-independent growth. The five pools of glutamine-independent variant cell lines were successfully expanded in glutamine-free selective medium (G-DMEM). The results obtained are summarised in Table 1 below.

TABLE 1

| Cell Line | No. of glutamine-independent colonies/$10^6$ cells |
|---|---|
| A1 | 20 |
| A2 | 0 |
| A3 | 0 |
| A4 | 0 |
| A5 | 0 |
| A6 | 0 |
| B1 | 12 |
| B2 | 0 |
| B3 | 0 |
| B4 | 0 |
| B5 | 1 |
| B6 | 8 |
| C1 | 0 |
| C2 | 0 |
| C3 | 20 |
| C4 | 0 |
| C5 | 0 |
| NS0 | 0 |

In order to test whether the glutamine-independent variants which arose in NS0 cells transfected with pRS3GSne18 resulted from vector amplification, genomic DNA was prepared from 3 cell lines (A1, B1 and B6) and from the corresponding pools of glutamine-independent variants (A1-gln, B1-gln and B6-gln). These DNA samples were used to determine the copy number of both vector and cellular GS genes by Southern blot analysis as follows. 5 µg of genomic DNA from each cell line was digested with BglI and BglII restriction enzymes and subjected to electrophoresis on a 1% agarose gel. A Southern blot of this gel was probed with a 0.5 kb PstI fragment spanning the 5' region of a hamster GS cDNA, isolated from pGSC45 (see FIG. 2). Plasmid pGSC45 is described in [8].

DNA samples from untransfected NS0 cells and cells transfected with the vector pST-6 [5] were also included as controls. The endogenous cellular GS genes are detected as a band of approximately 5 kb and a doublet at approximately 2.8 kb in each lane including the NS0 DNA sample. DNA from cell line 6A1 [5], which is transfected with the vector pST-6, shows an additional 1.4 kb band detected with the GS probe. This band is of the predicted size for a BglII fragment containing the vector GS-DNA (see FIG. 2). DNA from cell line 6A1-100-3, a clone derived from 6A1 by selection for GS-amplification using 100 µM Msx (as described in [5]) also shows the 1.4 kb vector GS band which is increased in intensity relative to the DNA from cell line 6A1, indicating vector amplification as a result of selection with Msx. A similar degree of amplification is observed in the vector band in the A1-gln pool relative to the original A1 cell line, indicating that vector amplification has again been selected, but in this case without the requirement for Msx.

From a number of other Southern blots, the vector copy number in cell line 6A1 has been estimated to be about 1 copy/cell and in 6A1-100-3 to be about 4 copies/cell. By comparison, the degree of amplification after selection for glutamine-independent variants of A1 is about 2–4 fold. The intensity of the bands due to the cellular GS genes is the same in each lane, indicating that there is no significant amplification of the endogenous genes. These bands therefore serve as a control for loading of similar quantities of DNA in each lane of the gel.

DNA from cell lines B1, B-gln, B6 and B6-gln show the expected vector-derived bands. However, there is no detectable vector amplification in the glutamine-independent variant pools from either B1 or B6 indicating that screening by Southern blotting or an equivalent technique is helpful in identifying amplified cell lines.

Nevertheless the 2-fold amplification observed in the A1-gln pool is significant, since the results will be the average for the many separate clones in the pool. To test whether individual clones within the pool had higher vector copy numbers, the A1-gln pool was cloned out by limiting dilution cloning. 10 separate glutamine-independent cell clones were expanded in culture and DNA from these clones was analysed by Southern blotting. A number of sub-clones of the A1-gln pool show a higher vector copy number than the average for the pool. Thus clones 1, 2, 6 and 8 show significant vector amplification and, from dilutions of vector DNA run on the same gel, the copy number in clones 1 and 8 was estimated to be between 5 and 10 copies/cell.

EXAMPLE 2 pEE14ne was linearised by digestion with SalI or BamHI and introduced into NS0 cells, as described in Example 1. 11 G418-resistant transfectant lines were selected, expanded in culture and transferred to glutamine-free medium as described in Example 1. Each of the 11 cell lines showed extensive cell death within 4–5 days of addition of G-DMEM, indicating that the vector GS-gene expression was inadequate of sustain glutamine-independent growth. After 2–3 weeks, the number of glutamine-independent variant colonies arising from each cell line was scored and the results are shown in Table 2 below.

TABLE 2

| Cell Line | No. of colonies.10⁷ cells plated |
|---|---|
| B-2A1 | 0 |
| S-C3 | 0 |
| S-C1 | 0 |
| B-D3 | 0 |
| S-A1 | 0 |
| S-A2 | ~$10^4$ |
| B-D1 | 2 |
| B-A1 | 0 |
| B-A6 | 0 |
| S-D6 | 0 |
| B-B6 | 0 |

Two cell lines, S-A2 and B-D1, generated glutamine-independent variants. Thus the vector pEE14ne can also be used to generate rare variants of initial transfected lines which can grow without glutamine. It is likely that by screening of pools or sub-clones of such variant lines by Southern blot analysis, cell lines containing amplified copies of the vector will be identified. The frequency with which transfected cell lines are generated using pEE14ne (2 out of 11 cell lines) is less than the frequency obtained with pRS3GSne18 as shown in Table 1 (5 out of 17). This is not surprising because pEE14ne uses a weaker promoter in association with the GS coding sequence. Nonetheless, it shows that as long as a proper screening protocol is used, it is possible to identify variants in which amplification has taken place.

Thus, it is believed that the use of a marker gene (ne) in conjunction with a GS gene including a weak promoter, such as the SV40E promoter, provides a novel method for selection and amplification in glutamine-auxotrophic cells. This has the particular advantage that maintenance of amplification can be achieved merely by using a glutamine-free medium without the need to use toxic selective agents such as MTX aminopterin or Msx.

It will be appreciated that the present invention has been described above by way of example only and that variations and modifications may be made by the person skilled in the art without departing from the scope of the invention.

REFERENCES

[1] WO-A-87/04462

[2] EP-A-0 319 206

[3] Roberts and Axel, Cell, 29, 109–119, 1982.

[4] Israel and Kaufman, Nucleic Acids Research, 17, No. 12, 4589–4604, 1989.

[5] EP-A-0 338 841

[6] Bebbington and Hentschel, DNA Cloning, Volume III, Chapter 8, edited by D. M. Glover, 1987.

[7] EP-A-0 216 846

[8] Hayward et al., Nucleic Acids Research, 14, 999–1008, 1986.

We claim:

1. A method, for obtaining a eukaryotic cell containing in its DNA multiple copies of GS gene, comprising:
   transfecting a eukaryotic glutamine auxotroph with a GS gene;
   selecting transfected cells containing the GS gene; and
   culturing the selected transfected cells in a medium which lacks glutamine or in which the amount of glutamine is progressively depleted, in the absence of a toxic GS inhibitor;
   the GS gene being of a character such that, or the conditions employed during the culturing step being such that, the GS gene is so transcribed such that cells in which the GS gene has been amplified survive in preference to cells in which the GS gene has not been amplified.

2. The method of claim 1, wherein:
   in the GS gene, the GS coding sequence is under the control of a weak promoter;
   the eukaryotic glutamine auxotroph is also transfected with a gene for selectable marker; and
   in the selecting step, selection is carried out using the selectable marker in a medium containing glutamine.

3. The method of claim 2, wherein the selectable marker is the neo gene or the ne gene.

4. The method of claim 2, wherein the GS gene and the gene for the selectable marker are located on a single vector.

5. The method of claim 2, wherein the promoter is the SV40 early or SV40 late promoter.

6. The method of claim 1, wherein:

in the GS gene, the GS coding sequence is under the control of a regulatable promoter;

in the selection step, the transfected cells are cultured in a glutamine-free medium under conditions which cause the promoter to be up-regulated; and in the culturing step, the medium is a glutamine-free medium and the conditions are such that the promoter is down-regulated.

7. The method of claim 6, in which the regulatable promoter is a eukaryotic promoter in which the bacterial lac operator sequences have been inserted.

8. The method of claim 1, wherein the glutamine auxotroph is a lymphoid cell.

9. The method of claim 8, wherein the lymphoid cell is a myeloma or hybridoma cell line.

10. The method of claim 1, wherein the culturing step is carried out in a medium containing asparagine.

11. The method of claim 1, wherein the glutamine auxotroph is also transfected with a heterologous gene whereby cell lines containing multiple copies of the heterologous gene may be selected.

12. A method for maintaining multiple copies of a GS gene in the DNA of transfected eucaryotic host cells comprising culturing the transfected cells in a medium which lacks glutamine, the GS gene being of character such that, or the conditions employed during culture being such that, the GS gene is so transcribed such that cells containing the multiple copies of the GS gene are selected over cells in which copies of the GS gene have been eliminated from the host cell DNA.

13. A method according to claim 12, in which the transformant host cells are prepared by a method according to claim 1.

* * * * *

UNITED STATES PATENT AND TRADEMARK OFFICE
CERTIFICATE OF CORRECTION

PATENT NO. : 5,747,308
DATED : May 5, 1998
INVENTOR(S) : Christopher Robert Bebbington et al.

It is certified that error appears in the above-identified patent and that said Letters Patent is hereby corrected as shown below:

On the title page; Item [73], Assignee, delete "Celltech Therapeutics Limited. Berkshire. United Kingdom" and insert --Alusuisse Holdings A.G., Neuhausen am Rheinfall, Switzerland--.

Signed and Sealed this

Twelfth Day of January, 1999

Attest:

Attesting Officer

*Acting Commissioner of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

CTATTTGGAA CTCCCACTGG                    2 0